United States Patent [19]

Ku

[11] Patent Number: 4,480,130

[45] Date of Patent: Oct. 30, 1984

[54] PREPARATION OF ORTHO-(ALKYLTHIOMETHYL) ANILINES BY CATALYTIC SULFILIMINE REARRANGEMENT

[75] Inventor: Audrey Y. Ku, Chesterfield, Mo.

[73] Assignee: Monsanto Company, St. Louis, Mo.

[21] Appl. No.: 529,914

[22] Filed: Sep. 7, 1983

[51] Int. Cl.³ ............................................. C07C 85/00
[52] U.S. Cl. .................................................. 564/440
[58] Field of Search ........................................ 564/440

[56] References Cited

U.S. PATENT DOCUMENTS

| | | | |
|---|---|---|---|
| 3,894,034 | 7/1975 | Gassman et al. | 564/440 X |
| 3,954,797 | 5/1976 | Gassman et al. | 564/440 X |
| 3,960,926 | 6/1976 | Gassman et al. | 564/440 X |
| 3,985,756 | 10/1976 | Gassman et al. | 564/440 X |
| 4,035,375 | 7/1977 | Gassman et al. | 564/440 X |
| 4,209,464 | 6/1980 | Steinman et al. | 546/440 X |

OTHER PUBLICATIONS

Claus, "Tetrahedron Letters", No. 32, pp. 3607–3610, 1968.
Gassman, "Tetrahedron Letters", No. 6, pp. 497–500, 1972.
Johnson, "Tetrahedron Letters", p. 501, (1972).
Vilsmaier, "Tetrahedron Letters", p. 625 (1972).
Claus & Vilsmaier, "Tetrahedron Letters", No. 31, p. 505, (1975).
Claus et al., "Phosphorus and Sulfur, No. 1, pp. 11, 18 (1976) and references cited therein.

Primary Examiner—Paul F. Shaver
Attorney, Agent, or Firm—Robert B. Martin; Richard H. Shear

[57] ABSTRACT

This invention relates to a process for preparing ortho-(alkylthiomethyl) anilines by catalytic rearrangement of aromatic sulfilimines in an inert organic solvent. The sulfilimine can be prepared using any of the procedures available in the art. This invention particularly relates to a new class of sulfilimine rearrangement catalysts.

11 Claims, No Drawings

PREPARATION OF ORTHO-(ALKYLTHIOMETHYL) ANILINES BY CATALYTIC SULFILIMINE REARRANGEMENT

BACKGROUND OF THE INVENTION

1. Field of the Invention

This invention relates to a process for catalytically rearranging aromatic sulfilimines.

2. Description of the Prior Art

The preparation of ortho-(alkylthiomethyl) anilines from the corresponding anilines via sulfilimine intermediates is known. Claus, Tetrahedron Letters, p. 3607 (1968), describes the preparation of aromatic sulfilimines from anilines and dimethylsulfoxide in the presence of $P_2O_5$ in a base such as triethylamine. Claus, however, discloses thermally rearranging these sulfilimines to ortho-(methylthiomethyl) anilines. See also, Gassman, Tetrahedron Letters, p. 497 (1972) and Johnson, Tetrahedron Letters, p. 501 (1972). Gassman discloses the use of N-t-butylanilines to generate N-t-butyl-N-chloro anilines, generally employing an alkyl-hypochlorite, and subsequently sulfilimine salts with dimethyl sulfide. Upon treatment with a basic catalyst under anhydrous conditions the sulfilimine salts are converted to N-substituted ortho-(methylthiomethyl) anilines. Vilsmaier, Tetrahedron Letters, p. 625 (1972) describes the reaction of anilines with dimethyl sulfide and N-chlorosuccinimide to form sulfilimine hydrochloride salts. Vilsmaier here does not teach the rearrangement of the sulfilimine or its salt. Another method of preparation of sulfilimine salts is disclosed in Claus and Vilsmaier, Tetrahedron Letters 31, p. 505 (1975). This article, like the previous Vilsmaier article, discloses the reaction of anilines with dimethyl sulfide in the presence of N-chlorosuccinimide to form the sulfilimine hydrochloride salt. In the Claus and Vilsmaier reference the sulfilimine hydrochloride salt is neturalized with aqueous caustic but Claus and Vilsmaier do not disclose the rearrangement of the sulfilimine produced by this process. See also Gassman U.S. Pat. Nos. 3,894,034, 3,954,797, 3,960,962, 3,985,765 and 4,035,375. The Gassman patents generally relate to the preparation and essentially anhydrous rearrangement of sulfilimine salts using basic catalysts to produce ortho-(methylthiomethyl) anilines. Claus, et al., Phosphorus and Sulfur, 1, pp. 11, 18 (1976) (and references cited therein) and U.S. Pat. No. 4,172,095 describe sulfilimine rearrangement in the presence of alcohols such as ethanol or t-butanol.

The prior art processes for preparing ortho-(alkylthiomethyl) anilines via the sulfilimine route generally exhibit a number of drawbacks which make them undesirable for commercial scale conversion processes. These prior art sulfilimine formation and rearrangement reactions proceed satisfactorily at the laboratory scale but they employ reagents which are expensive, often dangerous, and difficult to work with on a larger scale. One of the most serious of these drawbacks is the generally held requirement for processing under anhydrous conditions and utilizing dry bases such as tertiary amines. Moreover, the rearrangement of sulfilimines to ortho-(alkylthiomethyl) anilines was thought to require high temperatures, the presence of alcohols or dry basic catalysts such as triethylamine.

Accordingly, it is an object of the present invention to provide a process for the catalytic rearrangement of aromatic sulfilimines which substantially avoids the drawbacks of the prior art.

It is another object of this invention to provide a process for catalytically rearranging aromatic sulfilimines using novel rearrangement catalysts.

It is also an object of the present invention to provide a new class of sulfilimine rearrangement catalysts that are easier to use and generally more efficient than the alcohols and organic bases used by the prior art.

SUMMARY OF THE INVENTION

In accordance with the foregoing objectives and others which will be readily apparent to those skilled in the art, the present invention provides a process for catalytically rearranging aromatic sulfilimines to the corresponding ortho-(alkylthiomethyl) aniline, which process comprises heating an aromatic sulfilimine in an inert organic solvent, in the presence of a minor amount of catalyst selected from the group consisting of:

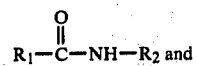

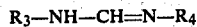

wherein

R₁ can be a hydrogen, a lower alkyl or an —NH—alkyl and R₂ can be a hydrogen, a lower alkyl, an aryl, or a

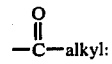

provided that $R_1$ and $R_2$ are not both hydrogens, or
$R_1$ and $R_2$ can be joined to form a cyclic compound having up to a 7-member ring, and
$R_3$ and $R_4$ can be a hydrogen, or a lower alkyl; provided that $R_3$ and $R_4$ are not both hydrogens, or
$R_3$ and $R_4$ can be joined to form a cyclic compound having up to a 7-member ring.

DETAILED DESCRIPTION OF THE INVENTION

The present invention provides a process for catalytically rearranging aromatic sulfilimines having the following general formula:

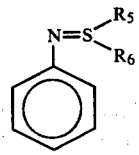

where $R_5$ and $R_6$ are both methyl groups; or where $R_5$ is methyl and $R_6$ is an aryl group; or where $R_5$ and $R_6$ are alkylene groups joined to form a 5- or 6-member ring. The aromatic sulfilimine may also contain one or more of a wide variety of nuclear substituents, as will be recognized by one skilled in this technology. Many of the aromatic sulfilimines have sufficient stability that their rearrangement does not occur under the conditions at which the sulfilimine is formed. Consequently, to effect rearrangement, such aromatic sulfilimines must either be heated for long periods of time at elevated temperatures, or they must be heated at somewhat reduced temperatures for shorter times in the presence of an appropriate catalyst. Unfortunately, the only catalysts disclosed by the prior art for catalyzing the rearrangement are alcohols such as ethanol; alkanolic alkali metal hyroxides such as methanolic potassium hydroxide; potassium t-butoxide and organic bases, such as tertiary amines, which require essentially anhydrous conditions for reasonable yield enhancement. In addition, the use of alcohols is generally undesirable in that it can lead to cleavage reactions which result in the formation of sulfoxides (e.g., dimethyl sulfoxides) and anilines (e.g., ortho-aminobenzotrifluoride).

The present invention provides a new class of sulfilimine rearrangement catalysts which do not require that the inert organic solvent containing the sulfilimine be completely dried because the rate of rearrangement is so fast that the competitive hydrolysis of the sulfilimine is a less important consideration. While applicant does not wish to be bound by any particular theroy, it is believed that the new class of rearrangement catalysts are particularly efficacious because such materials exhibit both acidic and basic characteristics.

The aromatic sulfilimine can be initially produced by any of the procedures available in the prior art as briefly outlined above. When a sulfilimine salt is initially prepared it must be treated to convert it to the corresponding neutral sulfilimine before catalytic rearrangement according to the process of this invention. A particularly desirable process for preparing a neutral sulfilimine is described in commonly assigned, copending application Serial No. 530,153 entitled "Preparation of 2-(Methylthiomethyl)-6-(Trifluoromethyl) Aniline from Ortho-Aminobenzotrifluoride" filed on even date herewith in the names of Chupp, Balthazor and Ku. This application is incorporated herein by reference. As long as the aromatic sulfilimine is substantially stable, i.e., as long as it is either stable in solution or can be isolated in substantially pure form, the present invention can be advantageously used to promote its rearrangement to the corresponding ortho-(alkylthiomethyl) aniline.

Aromatic dimethyl sulfilimines having the following structure are particularly suitable for use in connection with the present invention:

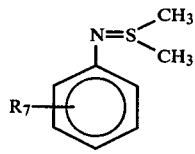

where $R_7$ can generally be selected from a variety of nuclear substituents including, for example, hydrogen, alkyl, alkoxy, alkoxyalkyl, alkenyl, alkenyloxy, alkynyl or alkynyloxy, aryl, aryloxy, aralkyl, or aralkyloxy, nitro, halogen, cyano of haloalkyl. A particularly preferred substituent in the ortho position is a trifluoromethyl group. The present invention will be described hereafter with specific reference to such S,S-dimethyl aromatic sulfilimines. However, as noted above, the catalytic rearrangement process of the present invention is broadly applicable for rearranging the above-described aromatic sulfilimines to form ortho-(alkylthiomethyl) anilines.

The sulfilimine rearrangement is carried out in an inert organic solvent. A wide variety of inert organic solvents may be employed including, for example, methylene chloride, ethylene dichloride, cyclohexane, heptane and toluene. A preferred solvent is ehtylene dichloride. The solvent used should not only be inert to the sulfilimine reactant and ortho-(methylthiomethyl) aniline product, but also should have some solubility for both the sulfilimine and the particular catalyst employed.

The sulfilimine is initially dissolved in the inert organic solvent and then a minor amount of the rearrangement catalyst is added. Depending upon the solubility of the particular catalyst in the inert organic solvent, generally about 0.5% to about 25% (by mol) is employed. Preferred catalysts can generally be employed at concentrations between about 1% and about 10% (by mol). The catalyst is selected from the group consisting of:

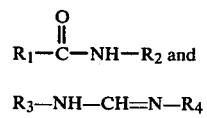

where $R_1$, $R_2$, $R_3$ and $R_4$ are defined as outlined above. Of the catalysts in this group, those having a high solubility in the particular inert organic solvent used are preferred. Succinimide is the preferred catalyst since it has a relatively high solubility in a wide variety of inert organic solvents. For example, if succinimide is used as a catalyst, only about 2 mol percent is generally required to achieve the desired catalytic effect. Besides succinimide, other preferred catalysts include imidazole, glutarimide, phthalimide, 2-pyrrolidone, 2-imidazolidone, and cyanuric acid. Generally, cyclic catalytic materials, i.e., compounds as outlined above, wherein the $R_1$ and $R_2$ or $R_3$ and $R_4$ substituents are joined together to form a ring, are generally preferred. In linear catalysts selected from the above-described groups, the length of the alkyl moiety in the catalyst is limited by solubility considerations. For the catalyst to be effective, it must be dissolved to a certain extent in the inert organic solvent wth the sulfilimine.

As noted above, the prior art describes the rearrangement of aromatic sulfimiline compounds to ortho-(alkylthiomethyl) anilines at elevated temperatures, in the presence of alcohols or in the presence of dry base catalysts. The present invention is based on the discovery that this new class of catalytic materials, in amounts of 0.5 to about 25% by mol, catalyze the rearrangement reaction permitting the reaction to proceed at an intermediate temperature and/or shorter reaction times.

In the broad practice of this invention, the catalyzed rearrangement step can be conveniently carried out over a wide range of temperatures. Typically, intermediate temperatures in the range of about 35° to 110° C. are preferred. Temperatures between about 60° and about 90° C. are particularly preferred. At these conditions, the rearrangement reaction is completed in about 0.5–20 hours, depending upon temperature and catalyst and sulfilimine concentrations. Generally, the rearrangement is complete in about 2–6 hours. Alternatively, a solution of sulfilimine, including, e.g., methylene chloride as a solvent, can be heated for short periods under pressure (i.e., autogenous to about 1000 psig) at 120°–180° C. to effect rearrangement. If desirable, catalyzed rearrangement temperatures of about 110° to 210° C. can be used to decrease the rearrangement times to a matter of minutes, with specific times depending upon temperature, catalyst and reactant concentrations. The sulfilimine rearrangement reaction is preferably conducted in a refluxing solvent as an easy way to control reaction conditions. The catalyst-containing inert organic solvent is typically heated at 80°-110° C. for about 1 to 4 hours, preferably about 75 to 85 minutes. Under these conditions, the rearrangemet should generally be complete.

The present invention generally provides high yields of the rearranged product. Yields from sulfilimine of about 92% ortho-(methylthiomethyl) aniline are typical. If desired, the rearrangement product may be purified by distillation. Prior to effecting this distillation or other treatment, the catalyst generally can be removed by art knwon techniques. For example, the succinimide can be removed by washing the organic phase with aqueous base, preferably sodium hyroxide solution. The presence of catalyst may result in undesired decompositon of the recovered aniline during purification by distillation. The inert organic solvent, e.g., ehtylene dichloride, can be removed from the washed organic phase by distillation at room temperature under reduced pressure.

The following examples are included for illustrative purposes only and are not intended to limit the scope of the invention.

EXAMPLE 1

This example describes attempts at rearranging N-(2-trifluoromethylphenyl)-S,S-dimethyl sulfilimine with and wthout the presence of succinimide as a catalyst. Sulfilimine (4.42 g), prepared by reacting ortho-aminobenzotrifluoride with dimethyl sulfide and N-chlorosuccinimide, was slurried in 10 ml of heptane and heated at reflux. After 1 hour at reflux, product analysis using nuclear magnetic resonance (NMR) spectroscopy indicated that less than 10% rearrangement had occured. About 5% by mol succinimide (0.1 g) was added to the cooled reaction mixture and upon reheating to reflux, the sulfilimine was completely rearranged to 2-(methylthiomethyl)-6-(trifluoromethyl) aniline MTA in less than about 10 minutes as verified by NMR spectroscopy.

EXAMPLE 2

This example also describes attempts at rearranging N-(2-trifluoromethylphenyl)-S,S-dimethyl sulfilimine with and without the presence of succinimide. Succinimide-free sulfilimine was heated at reflux in cyclohexane for about 4 hours. Fluorine NMR spectroscopy showed that no significant amounts of MTA were formed during this time. Succinimide (0.5 mol percent) was then added to the reaction mixture. Reflux was continued, and after about 3 hours rearrangement was complete as indicated by Fluorine NMR spectroscopy.

The following examples also pertain to the catalytic rearrangement of N-(2-trifluoromethylphenyl)-S,S-dimethyl sulfilimine, hereinafter referred to just as sulfilimine.

EXAMPLE 3

To a stirred solution containing 22.1 g of sulfilimine and 60 ml of ethylene dichloride was added 0.1 g of succinimide. The reaction mixture was heated at reflux for 2 hours. At the end of this period, a sample was withdrawn for NMR analysis and showed complete rearrangement of sulfilimine to MTA. GC analysis indicated 91% of MTA and 4% o-aminobenzotrifluoride (OABT) by hydrolysis of sulfilimine during the rearrangment).

EXAMPLE 4

The procedure of Example 3 was substantially repeated except that phthalimide was substituted for the succinimide with similar results observed.

EXAMPLE 5

A solution containing 4.41 g of sulfilimine, 10 ml of ethylene dichloride, and 0.15 g of imidazole was heated at reflux for 4 hours. At the end of this time, a sample was withdrawn for NMR analysis and showed complete rearrangement of sulfilimine to MTA.

EXAMPLE 6

A mixture of 4.41 g of sulfilimine, 10 ml of ehtylene dichloride, and 0.15 g of 2-pyrrolidone was heated at reflux for 4 hours. MTA (about 90%) plus a small amount of OABT (about 5%) were obtained at the end of this period.

EXAMPLE 7

A mixture of 2.21 g of sulfilimine, 10 ml of chloroform, and 0.2 g of 2-imidazolidone was heated at reflux for 12 hours. Not all of the imidazolidone dissolved in the chloroform. Subsequent analysis indicated that all sulfilimine was converted to MTA.

EXAMPLE 8

A mixture of 2.21 g of sulfilimine, 0.3 g of cyanuric acid and 10 ml of ehtylene dichloride was heated at 80° C. for 24 hours in order to complete the rearrangement reaction. The catalyst did not completely dissolve in the reaction mixture.

EXAMPLE 9

A mixture containing 4.42 g of sulfilimine, 40 ml of ethylene dichloride and 0.5 g of glutarimide was heated at reflux for 6 hours. All sulfilimine was converted to MTA at the end of 6 hours.

NOTE: In Examples 5-9 about 3-5% hydrolysis product OABT was formed in each case.

EXAMPLE 10

A mixture containing 4.42 g of sulfilimine in 10 ml of ethylene dichloride and 0.2 g of ortho-(trifluoromethyl) acetanilide was heated at reflux. All the sulfilimine was converted to MTA at the end of 8 hours.

Since modifications will be apparent to those skilled in the art, it is intended that the invention be limited only by the scope of the appended claims.

I claim:

1. A process for catalytically rearranging aromatic sulfilimines to the corresponding ortho-(alkylthiomethyl)aniline, which process comprises heating an aromatic sulfilimine in an inert organic solvent, in the presence of a minor amount of catalyst selected from the group consisting of:

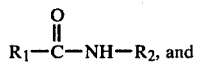

wherein $R_1$ can be a hydrogen, a lower akyl or an $-NH-$alkyl and $R_2$ can be a hydrogen, a lower alkyl, aryl or a

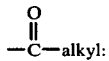

provided that $R_1$ and $R_2$ are not both hydrogens, or $R_1$ and $R_2$ can be joined to form a cyclic compound having up to a 7-member ring, and $R_3$ and $R_4$ can be a hydrogen, or a lower alkyl; provided that $R_3$ and $R_4$ are not both hyrogens, or $R_3$ and $R_4$ can be joined to form a cyclic compound having up to a 7-member ring.

2. The process of claim 1 wherein said aromatic sulfilimine is a dimethyl sulfilimine.

3. The process of claim 1 wherein said aromatic sulfilimine is a methyl-aryl sulfilimine.

4. The process of claim 3 wherein said methyl-aryl sulfilimine is a methyl-phenyl sulfilimine.

5. The process of calim 1 wherein said catalyst is selected from the group consisting of succinimide, imidazole, glutarimide, phthalimide, 2-pyrrolidone, 2-imidazolidone and cyanuric acid.

6. The process of claim 5 wherein said catalyst is succinimide.

7. The process of claim 1 wherein said sulfilimine is heated at an intermediate temperature in the range of about 35° to about 210° C.

8. The process of claim 7 wherein the temperature is in the range of about 60° to about 90° C.

9. The process of claim 1 wherein said catalyst is present at about 0.5 to about 25%, by mol.

10. The process of claim 9 wherein the catalyst is present at about 1 to about 10%, by mol.

11. The process of claim 1 wherein said inert organic solvent is ethylene dichloride.

* * * * *